United States Patent
Johnson et al.

(10) Patent No.: US 7,692,051 B2
(45) Date of Patent: *Apr. 6, 2010

(54) PROCESS FOR LIQUID PHASE HYDROGENATION

(75) Inventors: Marvin M. Johnson, Bartlesville, OK (US); Edward R. Peterson, Pearland, TX (US); Sean C. Gattis, Sugarland, TX (US)

(73) Assignee: Synfuels International, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/114,088

(22) Filed: May 2, 2008

(65) Prior Publication Data

US 2008/0300437 A1 Dec. 4, 2008

Related U.S. Application Data

(63) Continuation of application No. 11/383,325, filed on May 15, 2006, now Pat. No. 7,408,091.

(51) Int. Cl.
*G07C 5/02* (2006.01)
*G07C 5/08* (2006.01)

(52) U.S. Cl. ............... 585/259; 585/258; 585/261; 585/275; 585/833; 502/100; 502/102; 502/103; 502/104; 502/300; 502/301; 502/325; 502/328; 502/406

(58) Field of Classification Search ........... 585/259, 585/258, 261, 275, 833; 502/100, 102, 103, 502/104, 300, 301, 325, 328, 400, 406
See application file for complete search history.

(56) References Cited

U.S. PATENT DOCUMENTS

| | | | | |
|---|---|---|---|---|
| 2,848,510 A | * | 8/1958 | Myers et al. | 208/137 |
| 3,274,286 A | * | 9/1966 | Reich | 502/245 |
| 3,755,488 A | * | 8/1973 | Johnson et al. | 585/273 |
| 4,493,906 A | * | 1/1985 | Couvillion | 502/346 |
| 4,705,906 A | * | 11/1987 | Brophy et al. | 585/262 |
| 5,332,705 A | * | 7/1994 | Huang et al. | 502/53 |
| 5,356,851 A | * | 10/1994 | Sarrazin et al. | 502/185 |
| 5,510,550 A | * | 4/1996 | Cheung et al. | 585/259 |
| 6,340,429 B1 | | 1/2002 | Minkkinen et al. | |
| 6,350,717 B1 | * | 2/2002 | Frenzel et al. | 502/330 |
| 6,509,292 B1 | * | 1/2003 | Blankenship et al. | 502/330 |
| 7,045,670 B2 | * | 5/2006 | Johnson et al. | 585/259 |
| 7,408,091 B2 | * | 8/2008 | Johnson et al. | 585/259 |
| 2002/0004622 A1 | * | 1/2002 | Dai et al. | 585/260 |
| 2002/0028745 A1 | * | 3/2002 | Krylova et al. | 502/326 |

* cited by examiner

*Primary Examiner*—Walter D Griffin
*Assistant Examiner*—Huy-Tram Nguyen
(74) *Attorney, Agent, or Firm*—Conley Rose, P.C.

(57) ABSTRACT

A process and catalyst for the liquid phase selective hydrogenation of alkynes to alkenes with high selectivity to alkenes relative to alkanes, high alkyne conversion, and sustained catalytic activity comprising a reactant comprising an alkyne and a non-hydrocarbon solvent/absorbent, contacting the reactant stream with a hydrogen-containing stream in the presence of a supported, promoted, Group VIII catalyst, removing the solvent/absorbent, and recovering the alkene product.

16 Claims, 1 Drawing Sheet

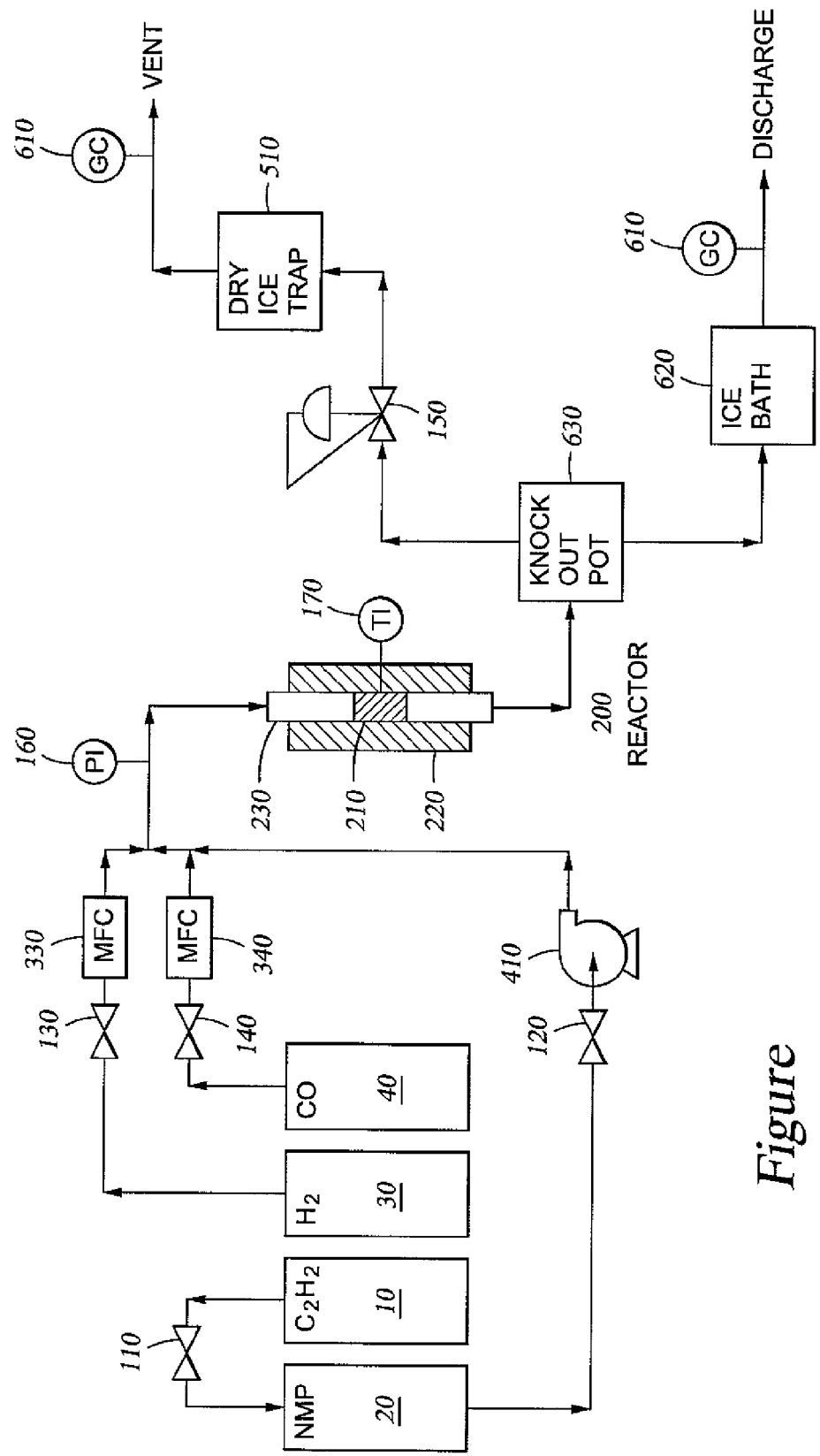
Figure

PROCESS FOR LIQUID PHASE HYDROGENATION

CROSS-REFERENCE TO RELATED APPLICATIONS

The present application is a continuation of U.S. Ser. No. 11/383,325 filed May 15, 2006, now U.S. Pat. No. 7,408,091 and entitled "Process for Liquid Phase Hydrogenation." which claims the benefit of U.S. Provisional Application Ser. No. 60/499,839 entitled "Catalyst Formulation for Hydrogenation" and U.S. Provisional Application Ser. No. 60/499,841, entitled "Process for Liquid Phase Hydrogenation" both filed Sep. 23, 2003, and incorporated herein by reference in their entirety for all purposes.

STATEMENT REGARDING FEDERALLY SPONSORED RESEARCH OR DEVELOPMENT

Not Applicable.

BACKGROUND OF THE INVENTION

1. Field of the Invention

This invention relates generally to the selective hydrogenation of unsaturated compounds to more-saturated analogs. In particular, alkynes are converted to alkenes by hydrogenation of the alkynes over a fixed bed of supported catalyst, while in an absorptive non-hydrocarbon absorbent.

2. Description of the Related Art

Hydrogenation of alkynes and/or multifunctional alkenes to compounds containing only one alkene group is an important industrial process and is discussed widely in the patent literature. Acetylene, the simplest alkyne, occurs in many processes as a main product or by-product which is thereafter converted to ethylene or ethane by hydrogenation. Thermal cracking of ethane can be caused to produce mostly ethylene, but a minor undesired product is acetylene. Pyrolysis of simple alkanes or mixtures containing primarily alkanes and partial oxidation of simple alkanes or mixtures containing primarily alkanes can be made to produce various blends that contain as principal products both alkenes and alkynes. Products in lower abundance will often include diolefins, compounds containing both yne and ene functionalities, polyenes, and other unsaturated moieties. Most commonly the desired products are the singly dehydrated compounds containing a single ene functionality. Thus, it is desirable to convert the alkynes to alkenes, but not convert the desired alkenes further to alkanes. Reactions of alkenes are generally more controllable than those of alkynes and diolefins, which tend to create oligomers and undesirable polyfunctional compounds.

The hydrogenation step is normally carried out on the primary gas produced in the cracking or pyrolysis reaction of natural gas and low molecular weight hydrocarbons, which includes all the initial gas products, also known as "front-end" hydrogenation, or subsequent to fractionation of the gas components, wherein the only stream subjected to hydrogenation is enriched in the highly unsaturated compounds, also known as "tail-end" hydrogenation. The advantage of primary gas hydrogenation is generally an abundance of the hydrogen required for hydrogenation. However, the excess available hydrogen in front-end hydrogenation can result in "run-away" reactivity wherein conversion of alkenes to alkanes reduces the value of the product. Fractionation reduces the available hydrogen but polymer formation is common, the effect of which is to shorten the useful life of the catalyst.

There are numerous examples of gas-phase hydrogenation of alkynes. For example, U.S. Pat. No. 6,127,310 by Brown, et al. teaches that the selective hydrogenation of alkynes, which frequently are present in small amounts in alkene-containing streams (e.g., acetylene contained in ethylene streams from thermal alkane crackers), is commercially carried out in the presence of supported palladium catalysts in the gas-phase.

In the case of the selective hydrogenation of acetylene to ethylene, preferably an alumina-supported palladium/silver catalyst in accordance with the disclosure in U.S. Pat. No. 4,404,124 and its division U.S. Pat. No. 4,484,015 is used. The operating temperature for this hydrogenation process is selected such that essentially all acetylene is hydrogenated to ethylene (and thus removed from the feed stream) while only an insignificant amount of ethylene is hydrogenated to ethane. Proper temperature selection and control results in minimization of ethylene losses and allows one to avoid a runaway reaction, which is difficult to control.

U.S. Pat. No. 5,856,262 describes use of a palladium catalyst supported on potassium doped silica wherein acetylene ranging in concentration from 0.01% to 5% in blends of ethylene and ethane is converted to ethylene in the gas-phase. U.S. Pat. No. 6,350,717 describes use of a palladium-silver supported catalyst to hydrogenate acetylene to ethylene in the gas-phase. The acetylene is present at levels of 1% in a stream of ethylene. U.S. Pat. No. 6,509,292 describes use of a palladium-gold catalyst wherein acetylene contained in a stream of principally ethylene, hydrogen, methane, ethane and minor amounts of carbon monoxide converts acetylene to ethylene in the gas-phase.

U.S. Pat. No. 6,395,952 describes recovery of olefins from a cracked gas stream using metallic salts and ligands. The cracked gas stream is hydrogenated prior to scrubbing to remove acetylene from the stream.

U.S. Pat. No. 5,587,348 describes hydrogenation of $C_2$ to $C_{10}$ alkynes contained in comparable streams of like alkenes over a supported palladium catalyst containing fluoride and at least one alkali metal. Examples show hydrogenation of low concentrations of acetylene, below 1%, being converted to ethylene in a gas principally comprised of methane and ethylene at 200 psig and 130° F. and 180° F. Care was taken to avoid heating the gas to a runaway temperature, wherein at least 4.5% of the ethylene would be converted to ethane and the temperature would become uncontrollable, which varied from about 70° F. to 100° F. above the minimum temperature that would reduce the acetylene concentration to acceptable levels.

U.S. Pat. No. 6,578,378 describes a complex process for purification of ethylene produced from pyrolysis of hydrocarbons wherein the hydrogenation follows the tail-end hydrogenation technique. At the top of the de-ethanizer the vapor of the column distillate is treated directly in an acetylene hydrogenation reactor, the effluent containing virtually no acetylene being separated by a distillation column called a demethanizer, into ethylene- and ethane-enriched tail product. The vapor containing acetylene is exposed to selective hydrogenation to reduce acetylene content of the principally ethylene gas or treated with solvent to remove it and preserve it as a separate product. In all cases the acetylene content of the pyrolysis gas contained less than 1.5 mol % acetylene.

Hydrogenation is also known to occur in the liquid phase where the fluids are easily conveyed or transported as liquids under reasonable temperature and pressure. Naphtha cracking produces significant quantities of $C_4$ and $C_5$ unsaturated compounds, with 1,3 butadiene and 1-butene generally having the greatest commercial value.

U.S. Pat. No. 6,015,933 describes a process in which polymer by-products from the steam cracking of naphtha to butadiene are removed. Acetylenes in the liquid hydrocarbon stream are selectively hydrogenated in a reactor to produce a reactor product containing at least hydrogen, butadiene, and polymer by-products having from about 8 to about 36 carbon atoms, and typically containing butenes and butanes. The acetylenic compounds are primarily vinyl acetylene, ethylacetylene, and methylacetylene. These acetylene group-containing molecules are converted to 1,3 butadiene, 1-butene, and propylene, but can react further with butadiene to form polymeric by-products. The reaction is carried out in the liquid phase with butadiene as the carrier. The undesirable feature of this process is that the carrier reacts with the products of the hydrogenation reaction, necessitating the removal of the polymeric by-products described.

U.S. Pat. No. 5,227,553 describes a dual bed process for hydrogenating butadiene to butenes. This improvement is said to increase selectivity in streams containing high concentrations of butadiene while reducing the isomerization of butene-1 to butene-2, and nearly eliminating the hydrogenation of isobutene to isobutane as well as oligomerization.

U.S. Pat. No. 4,547,600 discloses the need for more silver than previously thought necessary in the hydrogenation of acetylenic compounds that are found in butadiene as a result of steam cracking. The reaction is performed in the liquid phase where the product is the carrier.

U.S. Pat. No. 3,541,178 reports a reduction in the loss of butadiene along with nearly complete reduction of acetylenic compounds by restricting the flow of hydrogen to no more than 80% to 90% of saturation in the hydrocarbon stream. This reduces the potential for polymerization of the vinylacetylenes, as there is no hydrogen remaining in the reaction stream at the end of the reaction. The undesirable aspect of this reduced hydrogen content however, is that the concentration of the hydrogen in the reactor is reduced, which decreases the reaction rate.

U.S. Pat. No. 3,842,137 also teaches a reduction in the loss of butadiene to butene along with nearly complete conversion of vinylacetylene to butadiene, through the use of an inert diluent gas for the hydrogen. The hydrogen-containing gas includes no more than 25% hydrogen. The reaction takes place in the liquid phase, between a temperature of 40° F. and 175° F., and at a pressure of 80 to 200 psig. Again however, an undesirable aspect of using a diluent is that concentration of the hydrogen in the reactor is reduced, which decreases the reaction rate.

U.S. Pat. No. 4,469,907 teaches high conversions of multiply unsaturated hydrocarbons to singly unsaturated hydrocarbons without subsequent isomerization, by staging the insertion of hydrogen into one or more reactors in series. An undesirable aspect of using several reactors however, is the increased complexity of the process, resulting in increased cost and more complicated process control.

There are several examples where non-linear and/or non-hydrocarbon compounds are hydrogenated in the liquid phase. For example, U.S. Pat. No. 5,696,293 describes liquid phase hydrogenation and amination of polyols, carried out at pressures below 20 MPa using a supported ruthenium catalyst and containing another metal from Groups VIA, VIIA, and VIII. A ruthenium-palladium or singly palladium catalyst is listed in the examples. An undesirable feature of this process is the need to filter the fine and expensive catalyst out of the product. Catalyst losses are potentially very costly.

U.S. Pat. No. 5,589,600 discloses hydrogenation of benzene to cyclohexene using ruthenium-nickel catalysts in the presence of water, which is purported to improve selectivity.

U.S. Pat. No. 5,504,268 discloses hydrogenation of aromatic acetylenic compounds that are impurities in vinyl aromatic compounds, over a supported palladium catalyst. The purported improvement is obtained via reduction of the hydrogen concentration by using a gas phase diluent such as nitrogen or methane. As previously noted, an undesirable aspect of using a diluent however, is the reduction in the concentration of hydrogen in the reactor and corresponding decrease in the reaction rate.

Carbon monoxide is known to enhance hydrogenation selectivity. It is added to a stream that has been thermally cracked or pyrolyzed to reduce the hydrogenation of the ene functional groups. U.S. Pat. No. 6,365,790 describes an approach to selective hydrogenation of $C_{10}$ to $C_{30}$ alkynes to their respective alkenes in the liquid phase, by careful addition of a compound that decomposes to form CO. An undesirable aspect of using an additive is that the additive must later be removed from the product in diminished form.

U.S. Pat. No. 4,517,395 indicates that CO and $H_2$ added to a liquid phase of $C_{3+}$ multi-ene or mono-yne hydrocarbons, dispersed in the single-ene containing hydrocarbons, results in improved conversion due to better selectivity. The emphasis is on maintaining sufficient pressure to hold the CO and $H_2$ in the liquid phase rather than dispersed as a heterogeneous phase. Notably, water is added to reduce the amount of CO required as well as to reduce the temperature required.

U.S. Pat. No. 4,705,906 presents a catalyst formulation wherein acetylene is converted by hydrogenation to ethylene, in the presence of CO in concentrations greater than 1 vol % in a temperature range between 100° C. and 500° C. The catalyst is a zinc oxide or sulphide, which may incorporate chromium, thorium, or gallium oxide. Zinc oxide and zinc sulphide were reportedly chosen for the reason that, although palladium catalysts are reasonably tolerant of the usual organic impurities which act solely as activity moderators, palladium catalysts are poisoned at low temperatures by high concentrations of carbon monoxide, such as those associated with unsaturated hydrocarbon-containing products obtained by the partial combustion of gaseous paraffinic hydrocarbons. This is to be contrasted with their behavior at low carbon monoxide concentrations, typically at concentrations less than 1 vol %, at which moderation of catalytic activity is reported to enhance the selectivity of acetylene hydrogenation to ethylene. At high temperature, palladium catalysts are active even in the presence of carbon monoxide, but selectivity of acetylene hydrogenation to ethylene is drastically reduced by simultaneous hydrogenation of ethylene to ethane.

In U.S. Pat. No. 4,906,800, a Lindlar catalyst was used with a feed that contained no CO. The catalyst contained 5% palladium on a $CaCO_3$ support with about 3% lead as a promoter. After special treatment involving oxidation, reduction in CO, and finally a heat treatment step of the readily oxidized and reduced Lindlar catalyst, the treated catalyst showed improved selectivity at high conversion, but again at higher temperatures above 200° C. selectivity decreased significantly.

U.S. Pat. No. 5,847,250 describes a supported palladium catalyst employing a "promoter" from Groups 1 or 2 (in the New classification system; CAS Groups IA and IIA) and the palladium being supported on silica that has been pretreated to contain the promoter. The purported advantage is that no carbon monoxide is needed to provide increased selectivity because the selectivity-increasing effect of the carbon monoxide is strongly temperature dependent. Large temperature gradients in the catalyst bed therefore have an adverse effect on the selectivity when carbon monoxide is present. The reaction is performed in the gas phase in one or more beds with or without intermediate cooling or hydrogen gas addition. Acetylene content ranges from 0.01% to 5%. The reported selectivity ranges from 19 to 56%.

The use of liquid carriers has also been described in several patents for various reasons. For example, U.S. Pat. No. 4,137,267 describes the hydrogenation of alkyl aminoproprionitrile in the liquid phase, using hydrogen and ammonia as reactants over a supported catalyst and using an organic solvent. The solvent was selected to absorb excess heat by vaporizing at the process conditions, which is said to provide some temperature control. An undesirable aspect of employing a volatilizing solvent is the concomitant difficulty of employing this technique in a fixed catalyst bed.

U.S. Pat. No. 5,414,170 teaches selective hydrogenation of a stream from an olefin plant after operation of a depropanizer but prior to operation of a de-ethanizer or de-methanizer. The hydrogenation is performed on the mixed-phase propane rich ethylene stream, as well as subsequently on the vapor product. A method is described by which the acetylenes in the front end of an olefin plant process stream are hydrogenated in the presence of a liquid hydrocarbon. The propane liquids, initially separated out of the inlet process stream, are used later to cool and wash the product of the acetylene hydrogenation reactor by adding them to the acetylene-containing stream during hydrogenation. An undesirable aspect of this process is the need to fractionate the propane from the small amount of ethylene produced.

U.S. Pat. No. 5,059,732 discloses a process to hydrogenate effluent from a steam cracker containing ethylene, acetylene, propylene, propyne, propadiene, and butadiene, with hydrogen in the presence of a palladium or other noble metal catalyst by use of a gasoline cut as an inert carrier. The rationale for improved catalyst life is that the aromatic content of the gasoline carrier prevents plating out of the diolefins on the catalyst, which can otherwise polymerize and form gums that obstruct the other reactive components from getting to the catalyst surface. An undesirable aspect of this process however, is the need to fractionate the heavier hydrocarbon fraction from the small amount of ethylene produced, although this is not as serious a problem as when propane is used as the carrier.

Several patents disclose the use of solvents to separate the acetylenic fraction of a fluid stream from the other components. It is well known that dimethylformamide (DMF) and n-methyl-2-pyrrolidone (NMP) are good liquid absorbents for acetylene. Likewise, it is well known that DMF, furfural, ethylacetate, tetrahydrofuran (THF), ethanol, butanol, cyclohexanol, and acetonitrile are useful absorbents for 1,3-butadiene.

French Patent No. 2,525,210 describes a method for the purification of a stream containing mostly ethylene with a smaller amount of acetylene contaminant, wherein the acetylene is not converted to ethane. The basic concept is to hydrogenate a gas stream short of complete conversion, leaving some acetylene in the gas stream, then to absorb the acetylene in a solvent that extracts the acetylene from the ethylene stream. This extracted acetylene is separated from the solvent and recycled to the ethylene stream for hydrogenation. This is said to increase conversion to ethylene. An undesirable aspect of this process is the need to control the hydrogenation significantly below complete conversion.

U.S. Pat. No. 4,277,313 focuses on the purification of a $C_4$ stream containing acetylene compounds by hydrogenation of the acetylenic compounds followed by downstream separation. The hydrogenation step is carried out in the liquid phase after the hydrocarbon has been separated from the absorbing solvent. It is said to be important to remove the acetylenic compounds prior to polymerization since they can form explosive metal acetylides and will cause the polymer to be off-spec. Suitable inert solvents for this process purportedly include: dimethylformamide (DMF), furfural, ethylacetate, tetrahydrofuran (THF), ethanol, butanol, cyclohexanol, and particularly acetonitrile.

U.S. Pat. No. 3,342,891 describes fractionating a stream of $C_4$ and $C_5$ alkadienes into two streams, where one stream is reduced in vinyl acetylenes and the second stream is enriched in vinyl acetylenes. DMSO was used to separate the vinylacetylene from the enriched stream. The DMSO that contains the vinylacetylene was stripped with nitrogen to conentrate the vinylacetylene, which was subsequently hydrogenated in the gas phase. Unconverted vinyl acetylene in the effluent is recycled back to the feed of the fractionation column.

In some examples, the use of a liquid carrier or solvent is disclosed in which the liquid carrier or solvent is present during the hydrogenation step. U.S. Pat. No. 4,128,595 for example, teaches a process wherein gaseous acetylene or acetylene group containing compounds are contacted with hydrogen via an inert saturated liquid hydrocarbon stream with hydrogenation occurring over a typical Group VIII metal supported on a catalyst medium. Examples of inert saturated hydrocarbons include various hexanes, decanes and decalin. The process requires the acetylene containing compound and saturated hydrocarbon solvent be fed co-currently into the top of a trickle bed reactor because the solubility of the acetylene containing compound in the saturated hydrocarbon solvent is poor at reaction conditions. An undesirable aspect of this process is the poor solubility of the hydrocarbon solvent toward acetylene. This patent teaches that rapid catalyst deactivation can occur with polar solvents. Dimethylformamide (DMF) was used as an absorbent for ethylene and the polar solvent during hydrogenation. The result indicated rapid catalyst deactivation with conversion dropping from 100% to 50% over a period of 17 hours. Accordingly, there is substantial need for a practicable liquid phase hydrogenation process, using satisfactory non-hydrocarbon solvents, if sufficient selectivity and conversion can be provided.

As is apparent, an efficient, practicable process for liquid-phase selective hydrogenation, with sufficient conversion and selectivity, would be a substantial contribution to the art. It has now been found that high alkyne conversion can be obtained with significant improvement in the selectivity to the corresponding alkene relative to the alkane in accordance with the present invention. Surprisingly, and contrary to the teachings of the conventional art relating to use of a polar solvent, such as dimethylformamide, a progressive decline in catalyst activity with time on stream is not observed with the inventive process, and excellent selectivity is obtained. In particular, the present invention exhibits increasing acetylene conversion to high steady state values, while exhibiting excellent selectivity to ethylene, with sustained performance in operation for extended periods of time.

SUMMARY OF THE INVENTION

It is thus an object of this invention to overcome the deficiencies of the prior art and provide a process for the selective hydrogenation of acetylene and acetylenic compounds wherein the acetylene and/or acetylenic compounds are absorbed from a gas or liquid stream by use of a non-hydrocarbon absorbent liquid to provide a reactant stream. The reactant stream comprising the absorbent liquid containing the acetylene or acetylenic compounds is then exposed to a catalyst comprising a Group VIII metal (using the CAS classification system) or combination of such catalysts co-currently with a hydrogen-containing gas stream. It is consistent with this invention that other gas or liquid components may be present in the reactant stream that contains acetylene or acetylenic compounds, in major or minor proportions, and that these other components may include, without limitation, aromatics, olefins, alkanes, water, alcohols, oxides, sulfides, and amines. Typically, the non-hydrocarbon absorbents of this invention will be capable of absorbing in the range of about 0.01 to about 100 (vol/vol) acetylene and/or acetylenic compounds. It is also consistent with this invention that the non-hydrocarbon absorbents used to absorb acetylene or acetylenic compounds from the aforementioned gas stream may comprise, without limitation: n-methyl-2-pyrrolidone (NMP), acetone, tetrahydrofuran (THF), dimethylsulfoxide (DMSO), and monomethylamine (MMA), and that the temperature and pressure selected for hydrogenation of the acetylene or acetylenic compounds in the polar absorbent will be selected such that the liquid absorbent does not form significant vapor.

It is also an object of this invention to obtain useful conversion of acetylene at relatively moderate temperatures and pressures. Typically, the temperature may range from 0° F. to 400° F. and the pressure may range from 1 to 2000 psia, wherein the choice of operating conditions will vary depending on the absorbent chosen and the acetylenic compounds being hydrogenated, as will be known to those skilled in the art. The temperature and pressure conditions employed in this invention are typically sufficient to maintain the absorbent liquid in the liquid phase with at least a portion of the acetylene and/or acetylenic compounds contained in the absorbent being hydrogenated.

It is also an object of this invention that the acetylene and/or acetylenic compounds are selectively hydrogenated to ethylene or homologous ethenic compounds with minimum conversion to ethane and other saturated compounds.

It is also an object of this invention to provide operation of the reaction process in such a way that "run-away" temperature conditions do not occur, and that temperature control is naturally enhanced. The use of the aforementioned liquid absorbents acts to absorb more heat with less temperature rise, either at the catalyst surface or throughout the fluid phase, than a gas under most process conditions, due to a larger heat capacity per volume than the gas phase alone. These liquid absorbents also provide for improved heat transfer, as their thermal conductivity is much greater under most process conditions.

It is also an object of this invention to obtain useful conversion of acetylene even in the presence of carbon monoxide well in excess of 1% of the non-absorbent components.

It is also an object of this invention to obtain useful conversion of acetylene in the presence of hydrogen equal to or in excess of that stoichiometrically required to effect the total hydrogenation of the acetylene or acetylenic compounds.

It is also an object of this invention to perform absorption of acetylene from a mixed gas stream obtained from thermal or oxidatively enhanced cracking, prior to further separation of the gas components, in a commercially feasible manner.

It is also an object of this invention to perform the hydrogenation of acetylene and acetylenic compounds in one or more reactors in series. Any catalyst known to selectively hydrogenate acetylene can be employed by this invention. The Group VIII metal hydrogenation catalysts are generally used and preferred. Most commonly, these are employed as supported catalysts on such materials as an alumina, a silica, or an aluminosilicate, but they may be supported as well on metal meshes or screens. Most commonly, these supports contain one or more Group VIII metals in the amount of 0.01 to 10 percent by weight. There are many formulations of such catalysts which contain other components, primarily Group I through Group VII metals which improve selectivity, conversion, and/or yield. Accordingly, catalysts useful for the present invention may comprise Group VIII metal co-formulated with metals from Groups I through VII. Other applicable catalysts include but are not limited to nickel arsenide on alumina, ruthenium on alumina, Raney-nickel, zinc oxide, and zinc sulphide.

It is also an object of this invention to perform the hydrogenation in a liquid or dispersed phase, such that separation can be effected by conventional means including, without limitation: distillation, single stage flash, multistage flash, crystallization, washing with a solvent, partitioning with a non-solvent, or a combination of these common separation means, not exclusive of less common techniques that are known to those skilled in the art.

BRIEF DESCRIPTION OF THE DRAWING

The invention, together with further advantages thereof, may best be understood by reference to the following description taken in conjunction with the accompanying drawing in which:

The FIGURE is a simplified flow diagram of a selective hydrogenation process in accordance with the present invention.

DETAILED DESCRIPTION OF THE PREFERRED EMBODIMENTS

The present invention thus provides, in a preferred embodiment, a process for the selective hydrogenation of acetylene and/or acetylenic compounds wherein the acetylene and/or acetylenic compounds are absorbed from a gas or liquid stream by use of a non-hydrocarbon absorbent liquid to provide a reactant stream. Thereafter the reactant stream comprising the absorbent liquid, which contains the acetylene or acetylenic compounds, is exposed to one or more Group VIII catalysts or mixtures of known Group VIII catalysts that may be co-formulated with other metals, such as those from Groups I through VII, or other known hydrogenation promoting catalysts. The reactant stream may preferably be contacted with the catalyst(s) via any of the known reactor systems within the discretion of one skilled in the art, including, without limitation, slurry bubble column reactors, trickle bed reactors, three phase fluidized beds, fixed or moving bed reactors, riser reactors, fast-fluidized beds, or any other reaction system, so long as the reactant stream and catalyst are contacted under conditions suitable for hydrogenation and at a pressure and temperature sufficient to maintain the absorbent liquid in the liquid phase, with at least a portion of the acetylene and/or acetylenic compounds contained in the absorbent being hydrogenated, without departing from the scope of the invention. The size, capacity, and scope of any particular embodiment of the inventive process to be implemented may be determined following standard engineering practices well-known to those skilled in the art and following performance data presented herein.

The absorption step may typically be performed at a temperature in the range of about 0° F. to about 400° F., a pressure in the range of about 1 psia to 2000 psia, wherein hydrogen is furnished in sufficient quantity to hydrogenate at least a portion of the acetylene and/or acetylenic compounds. The non-hydrocarbon absorbent liquid is typically capable of absorbing in the range of about 0.01 to 100 vol/vol acetylene and/or acetylenic compounds at standard conditions of temperature and pressure (STP). Any of the conventional techniques to accomplish the absorption that are known to those skilled in the art may be employed without departing from the scope of the invention.

Carbon monoxide may be contained in a stream comprising hydrogen or a hydrogen-containing gas, or may be fed concurrently or simultaneously with the hydrogen required for hydrogenation, and is typically present in concentration in the range of about 0.01% to 300% of the stoichiometrically required amount of hydrogen.

The non-hydrocarbon liquid absorbent may comprise, without limitation: n-methyl-2-pyrrolidone (NMP), acetone, tetrahydrofuran (THF), dimethylsulfoxide (DMSO), monomethylamine (MMA), and/or combinations thereof, and is preferably NMP. The hydrogenation may preferably be effected by passing the absorbed acetylene and/or acetylenic compounds into the inlet of a fixed bed reactor, or a series of reactors, containing the catalyst, while co-currently passing a stream of gas containing at least hydrogen into the reactor at an inlet location.

The source of acetylene and/or acetylenic compounds and/or hydrogen and/or carbon monoxide may preferably be pyrolysis, thermal cracking, steam cracking, partial oxidation, or other like process, wherein hydrocarbons or hydrocarbon-containing streams are thermally and/or chemically modified to produce increased quantities of unsaturated components, and the acetylene and/or acetylenic compounds may comprise, but are not limited to: acetylene, allene, vinyl acetylene, methyl acetylene, ethyl acetylene, 1-butyne, 2-butyne, and 1,3-butadiyne.

The Group VIII catalyst or mixture of Group VIII catalysts which may be co-formulated with other metals such as those from Groups I through VII is preferably a supported catalyst comprising about 0.01% to 10% Group VIII metal or about 0.01% to 10% Group VIII metal and 0.01% to 10% Group I through Group VII metal. The catalyst may comprise Raney nickel, palladium on alumina, ruthenium on alumina, nickel arsenide on alumina, zinc oxide, zinc sulphide, and mixtures of one or more of the above, in addition to other catalysts as are known to those skilled in the art. The catalyst may also comprise palladium/gold on alumina or the Lindlar catalyst. In another embodiment, the catalyst may preferably be palladium/gallium on alumina and/or palladium/indium on alumina and/or palladium/zinc on alumina.

In another preferred embodiment, the reactant stream may be exposed to a catalyst or catalysts as described in our co-filed application Ser. No. 10/727,919, entitled "Catalyst Formulation for Hydrogenation" by Marvin M. Johnson, Edward R. Peterson, and Sean C. Gattis, hereby incorporated by reference herein in its entirety.

In another preferred embodiment, the present invention comprises a process for recovering hydrogenated product from the liquid absorbent by distillation, wherein the hydrogenated stream is passed into a distillation column that is operated such that at least 90% of the hydrogenated product is recovered as a gas from the top of the distillation column, as will be known to those skilled in the art.

In another preferred embodiment, the present invention further includes a process for recovering hydrogenated product from the liquid absorbent by staged flashing, wherein the hydrogenated stream is passed into a flash drum that is operated at a pressure and temperature such that at least 90% of the hydrogenated product is recovered as a gas from the top vent of the flash drum. More than one flash drum may be used at more than one set of pressure and temperature conditions, such that at least 90% of the hydrogenated product is recovered as a gas from the top vents of the flash drums.

In another preferred embodiment, the present invention includes a process for recovering hydrogenated product from the liquid absorbent by intimate mixing of the hydrogenated stream with a partitioning fluid such that the desired hydrogenated product is evolved from the absorbent liquid by exclusion due to the properties of the mixture, such that at least 90% of the hydrogenated product is recovered as a separate stream from the separator.

In another preferred embodiment, the present invention includes a process for recovering hydrogenated product from the liquid absorbent by distillation wherein the hydrogenated stream is passed into a distillation column operated such that at least 90% of the hydrogenated product is recovered as a liquid from the bottom of the distillation column.

In another preferred embodiment, the present invention includes a process for recovering hydrogenated product from the liquid absorbent by staged flashing, wherein the hydrogenated stream is passed into a flash drum operated at a pressure and temperature such that at least 90% of the hydrogenated product is recovered as a liquid from the bottom of the flash drum.

Additional and further variations of the embodiments of the present invention will be known to those of skill in the art based on the disclosure of the inventive process, and the application of such known engineering practice within the field of hydrogenation and, more particularly, the field of the selective hydrogenation of alkynes to their corresponding alkenes, to the aspects of the present invention should be considered to be within the scope of the present invention.

Referring now to the FIGURE, an acetylene solution of n-methyl-2-pyrollidone (NMP) was first prepared by slowly bubbling pure acetylene from acetylene vessel 10 at atmospheric pressure via valve 110 into a weighed and tared NMP vessel 20 containing NMP. The NMP containing acetylene was then drawn through valve 120 by pump 410 and pumped to reactor 200 comprising tubular reaction vessel 230 comprising a one-half inch (OD) stainless steel tube containing a supported catalyst 210. Co-currently, a gas containing hydrogen from vessel 30 and carbon monoxide from vessel 40 was flowed under pressure at a controlled rate using flow controllers 330 and 340, and corresponding control valves 130 and 140, and was mixed with the NMP stream containing acetylene from the outlet of pump 410. The fluid mixture comprising NMP, acetylene, hydrogen, and CO was allowed to flow at a controlled rate and under pressure control into reaction vessel 230 of reactor 200, containing the fixed bed of supported catalyst 210. The reactor temperature was controlled by an external heating element (not shown) surrounded by insulation 220. The fluid temperature was measured prior to its entering the reactor and upon leaving the reactor by temperature sensors (not shown). The reaction temperature was measured near the center of the fixed bed of catalyst 210 via a ⅛ inch thermowell and temperature indicator 170. Reactor pressure, indicated by pressure indicator 160 was controlled by a pressure control device (calibrated and self-regulating mechanical spring-type) 150. The reactor fluid cooled upon exiting the reactor, and a gas-liquid separation was made in knock-out pot 630 at 80° C. The overhead gas from knock-out pot 630 flowed through pressure control device 150, and was cooled to −79° C. in dry ice trap 510 to collect all remaining components except those that remain a gas at this temperature and pressure, such as hydrogen, nitrogen, argon, and methane, and was then sent to gas chromatograph 610 to provide quantitiative analysis of the gas composition. The liquid stream, comprising NMP, $C_2$, $C_4$, and heavier components was collected in knock-out pot 630, and was periodically sampled via ice bath 620, and was also analyzed by gas chromatograph 610 to obtain quantitative composition analysis.

To more clearly illustrate the present invention, several examples are presented below. These examples are intended to be illustrative and no limitations to the present invention should be drawn or inferred from the examples presented herein.

EXAMPLES

Selective Hydrogenation Catalyst Preparation

A number of experimental catalysts were prepared by incipient wetness impregnation of a commercially available "skin" catalyst (also known in the art as "rim" or "eggshell" catalysts) that contained from 0.3 to 0.7 wt-% palladium concentrated near the exterior surface of roughly spherical particles of alumina, which had been heat treated to reduce microporosity. For example, a commercially available catalyst originally available from Mallinckrodt Chemicals, product number E144SDU, containing about 0.5 wt-% Pd on roughly spherical $\frac{1}{16}$" diameter alumina particles, with a surface area of about 40-70 m$^2$/gm and a pore volume of about 0.5 may be used. Similar catalysts commercially available from Engelhard and Calsicat (such as 1435DU) may also be used. Several of the experimental catalysts described below were crushed and then double-screened between 40 and 50 mesh (USS or U.S. sieve series) screens, thus providing catalyst particles with a minimum dimension in the range of from about 0.0117 to about 0.0165 inches. Those skilled in the art will recognize that other known catalysts and supports may likewise be employed without departing from the scope of the invention. Most of the experimental catalysts described below involved dissolving the nitrate salt of the promoter in the amount of water required to just fill the internal pores of the catalyst support, though other techniques as are known in the art may of course be employed.

Example 1

Catalyst containing 0.3 wt-% Pd/Al$_2$O$_3$. A commercially available Engelhard catalyst that contained 0.3 wt-% Pd/Al$_2$O$_3$ was used for this Example. The alumina supported catalyst particles were roughly spherical and approximately $\frac{1}{16}$ inches in diameter. The catalyst was dried for one hour. The dried product was reduced in place at 100° C. and 250 psig for two hours with a 2:1 H$_2$:CO gas mixture (66% H$_2$-34% CO).

Example 2

Catalyst containing 0.3 wt-% Pd/Al$_2$O$_3$. Preparation of this catalyst began with the Engelhard catalyst of Example 1 that contained 0.3 wt-% Pd/Al$_2$O$_3$. The alumina supported catalyst particles were roughly spherical and approximately $\frac{1}{16}$ inches in diameter. The catalyst was dried for one hour, crushed and double-screened between 40 and 50 mesh (USS) screens, and reduced in place at 400° C. and 150 psig for one hour with a 2:1 H$_2$:CO gas mixture (66% H$_2$-34% CO).

Example 3

Catalyst containing 0.7 wt-% Pd/Al$_2$O$_3$. Preparation of this catalyst began with an Engelhard catalyst which contained 0.7 wt-% Pd/Al$_2$O$_3$. The alumina supported catalyst particles were roughly spherical and approximately $\frac{1}{16}$ inches in diameter. The catalyst was reduced in place at 50° C. and 250 psig for one hour with a 2:1 H$_2$:CO gas mixture (66% H$_2$-34% CO).

Example 4

Catalyst containing 0.3 wt-% Pd-1.2 wt-% Au/Al$_2$O$_3$. Preparation of this catalyst began with the Engelhard catalyst of Example 1 that contained 0.3 wt-% Pd/Al$_2$O$_3$. The alumina supported catalyst particles were roughly spherical and approximately $\frac{1}{16}$ inches in diameter. For this Example, the catalyst particles were dropwise impregnated with a gold chloride solution, dried at 150° C. for one hour, and calcined at 300° C. for one hour to produce a 1.2 wt-% Au-0.3 wt-% Pd/Al$_2$O$_3$ product. The product was crushed and double-screened between 40 and 50 mesh (USS) screens, and reduced in place for one hour at 100° C. and 250 psig with a 2:1 H$_2$:CO gas mixture (66% H$_2$-34% CO).

Example 5

Catalyst containing 0.3 wt-% Pd-0.3 wt-% Ag/Al$_2$O$_3$. Preparation of this catalyst began with a Calsicat catalyst that contained 0.3 wt-% Pd/Al$_2$O$_3$. The alumina supported catalyst particles were roughly spherical and approximately $\frac{1}{16}$ inches in diameter. For this Example, 10 grams of the Calsicat catalyst was dropwise impregnated with 0.047 grams of AgNO$_3$ dissolved in 5 ml of water, dried for one hour at 150° C., and calcined at 300° C. for one hour to give a 0.3% Ag-0.3% Pd/Al$_2$O$_3$ product. The product was then crushed and double screened between 40 and 50 mesh (USS) screens and reduced in place at 100° C. and 250 psig for one hour with a 2:1 H$_2$:CO gas mixture (66% H$_2$-34% CO).

Example 6

Catalyst containing 0.3 wt-% Pd-0.6 wt-% Ag/Al$_2$O$_3$. Preparation of this catalyst began with the Calsicat catalyst of Example 5 that contained 0.3 wt-% Pd/Al$_2$O$_3$. The alumina supported catalyst particles were roughly spherical and approximately $\frac{1}{16}$ inches in diameter. For this Example, the procedure of Example 5 was followed except that the concentration of silver nitrate in the impregnating solution was twice that of Example 5. The product was again dried for one hour at 150° C., and calcined at 300° C. for one hour. The 0.6% Ag-0.3% Pd/Al$_2$O$_3$ product was then crushed and double screened between 40 and 50 mesh (USS) screens, and reduced in place at 100° C. and 250 psig for one hour with a 2:1 H$_2$:CO gas mixture (66% H$_2$-34% CO).

Example 7

Catalyst containing 0.3 wt-% Pd-0.1 wt-% Mn/Al$_2$O$_3$. This catalyst was prepared from an Engelhard catalyst that contained 0.3 wt-% Pd/Al$_2$O$_3$. The alumina supported catalyst particles were roughly spherical and approximately $\frac{1}{16}$ inches in diameter. For this Example, the catalyst was dropwise impregnated with manganese acetate, dried at 150° C. and calcined at 300° C. to give a 0.3 wt-% Pd-0.1 wt-% Mn/Al$_2$O$_3$ product. The calcined product was then crushed and double screened between 40 and 50 mesh (USS) screens, and reduced in place at 300° C. and 250 psig for one hour with a 2:1 H$_2$:CO gas mixture (66% H$_2$-34% CO).

Example 8

Catalyst containing 0.3 wt-% Pd-0.385 wt-% In/Al$_2$O$_3$. This catalyst was prepared from the Engelhard catalyst that contained 0.3 wt-% Pd/Al$_2$O$_3$. The alumina supported catalyst particles were roughly spherical and approximately 1/16 inches in diameter. For this Example, the catalyst was dropwise impregnated with an aqueous solution of indium nitrate, dried at 150° C. for one hour, and calcined at 300° C. for one hour to give a 0.3 wt-% Pd-0.4 wt-% In/Al$_2$O$_3$ product. The calcined product was then crushed and double screened between 40 and 50 mesh (USS) screens, and reduced in place at 300-314° C. and 250 psig for one hour with a 2:1 H$_2$:CO gas mixture (66% H$_2$-34% CO).

Example 9

Catalyst containing 0.3 wt-% Pd-0.26 wt-% Ga/Al$_2$O$_3$. This catalyst was prepared from the Engelhard catalyst that contained 0.3 wt-% Pd/Al$_2$O$_3$. The alumina supported catalyst particles were roughly spherical and approximately 1/16 inches in diameter. For this Example, the catalyst was dropwise impregnated with an aqueous solution of gallium nitrate, dried at 150° C. for one hour, and calcined at 300° C. for one hour to give 0.3 wt-% Pd-0.26 wt-% Ga/Al$_2$O$_3$ product. The product was then crushed and double screened between 40 and 50 mesh (USS) screens, and reduced in place at 400° C. and 250 psig for one hour with a 2:1 H$_2$:CO gas mixture (66% H$_2$-34% CO).

Example 10

Catalyst containing 0.5 wt-% Pd-0.5 wt-% Zn/Al$_2$O$_3$. Preparation of this catalyst began with a palladium catalyst from Calsicat (product number E144SDU) containing 0.5 wt-% Pd/Al$_2$O$_3$. The alumina supported catalyst particles were roughly spherical and approximately 1/16 inches in diameter. The palladium-containing material was then dropwise impregnated with a solution of zinc formate, dried for one hour at 150° C., and calcined at 300° C. for one hour to give a 0.5 wt-% Pd-0.5 wt-% Zn/Al$_2$O$_3$ product. The product was then crushed and double screened between 40 and 50 mesh (USS) screens, and reduced in place at 400-420° C. and 250 psig for one hour with a 2:1 H$_2$:CO gas mixture (66% H$_2$-34% CO).

Selective Hydrogenation of Acetylene—Experimental Catalysts

Example 11

A reactor in accordance with an embodiment of the invention described above and in the drawing FIGURE was constructed for the tests described below. Approximately 3 cm$^3$ of catalyst was diluted with 6 cm$^3$ of inert low surface area alumina (alundum) as a catalyst surface area diluent, and placed into the reaction vessel in a fixed bed configuration. Other catalyst surface area diluents may of course be used, as will be known to those skilled in the art. The catalyst was placed in the center section of the reaction vessel between two six-inch deep beds of 3 mm glass beads, one placed upstream of the catalyst for preheat purposes and one downstream, in the exit section.

The operating conditions are as shown in Table 1. The liquid reactant flow rate was set at 18 ml/hr of NMP containing 4.2 wt-% dissolved acetylene. A 2:1 H$_2$:CO gas mixture was used and the H$_2$/C$_2$H$_2$ ratio was 1.56:1. Product gas analyses (for C$_2$ components only) were obtained after removal of the NMP and after the composition of the product gas had reached steady state and subsequent samples showed no significant change in composition. The gas composition results are shown in Table 1. The product gas concentrations do not sum to 100% due to the presence of other components in minor amounts and measurement error. The mass balance closure for these results is estimated at about 95%.

For comparison purposes, the selectivity of ethylene to ethane may be estimated by the ratio of the product ethylene concentration to the concentration of ethane, defined here as the screening selectivity $S_s$ (and presented in Table 1) as $S_s=[C_2H_4]/[C_2H_6]$. Also for comparison purposes, the relative acetylene conversions may be estimated from the product acetylene concentrations. This is defined here (and also presented in Table 1) as the screening conversion $S_c=100-[C_2H_2]$ where the acetylene concentration is expressed in percent.

The data shown in Table 1 thus describe representative results for catalytic selective hydrogenation in accordance with the invention. As may be seen from examination of the data tabulated in Table 1, significant improvements in the selectivity to ethylene result from the addition of promoters at high acetylene conversion. Contrary to the teachings of the prior art, a progressive decline in activity with time on stream was not observed. The gallium and indium containing catalysts showed relatively high selectivity. Likewise, excellent selectivity and activity were observed for catalysts prepared applying a promoter metal after first applying the Group VIII metal to the support. Accordingly, the catalytic process of the present invention provides improved conversion and selectivity in selective hydrogenation of acetylene dissolved in NMP. The indium-promoted catalyst and, to a lesser extent, the gallium-promoted catalyst is effective with palladium on alumina, and both exhibit higher selectivity to ethylene than either the traditional silver-promoted or gold-promoted catalysts used to advantage for the removal of acetylene in ethylene by selective hydrogenation in the front-end gas phase hydrogenation process.

TABLE 1

| Catalyst | Composition | T (° C.) | P (psig) | H$_2$/CO Flow (ml/min) | Ethane (%) | Ethylene (%) | Acetylene (%) | $S_s$ | $S_c$ (%) |
|---|---|---|---|---|---|---|---|---|---|
| Example 1 | 0.3% Pd on 1/16" alumina spheres | 111 | 250 | 30 | 10.0 | 89.4 | 0.5 | 8.9 | 99.5 |
| Example 2 | 0.3% Pd on 40-50 mesh alumina particles | 128 | 150 | 35 | 2.6 | 94.0 | 0.80 | 36 | 99.2 |
| Example 3 | 0.7% Pd on 1/16" alumina spheres | 111 | 250 | 40 | 6.4 | 93.4 | 0.1 | 15 | 99.9 |
| Example 4 | 0.3% Pd - 1.2% Au on 40-50 mesh alumina particles | 120 | 250 | 35 | 6.25 | 93.50 | 0.15 | 15 | 99.9 |
| Example 2 | 0.3% Pd on 40-50 mesh alumina particles | 119 | 250 | 32 | 2.42 | 91.0 | 6.34 | 38 | 93.7 |

TABLE 1-continued

| Catalyst | Composition | T (° C.) | P (psig) | H$_2$/CO Flow (ml/min) | Ethane (%) | Ethylene (%) | Acetylene (%) | S$_s$ | S$_c$ (%) |
|---|---|---|---|---|---|---|---|---|---|
| Example 5 | 0.3% Pd - 0.3% Ag on 40-50 mesh alumina particles | 114 | 250 | 30 | 3.68 | 93.5 | 2.77 | 25 | 97.2 |
| Example 6 | 0.3% Pd - 0.6% Ag on 40-50 mesh alumina particles | 115 | 250 | 30 | 3.33 | 96.2 | 0.41 | 29 | 99.6 |
| Example 7 | 0.3% Pd - 0.1% Mn on 40-50 mesh alumina particles | 122 | 250 | 30 | 3.91 | 95.6 | 0.42 | 24 | 99.6 |
| Example 8 | 0.3% Pd - 0.385% In on 40-50 mesh alumina particles | 137 | 250 | 30 | 1.46 | 96.8 | 1.70 | 66 | 98.3 |
| Example 9 | 0.3% Pd - 0.26% Ga on 40-50 mesh alumina particles | 130 | 250 | 30 | 2.02 | 97.5 | 0.40 | 48 | 99.6 |

Selective Hydrogenation of Acetylene-Sustained Activity of Indium-Promoted Palladium Catalyst Example 12

The results obtained from Example 11 and shown in Table 1 were considered promising. Therefore, an extended duration run was made with an indium-containing catalyst similar to that of Example 8 but with 0.22 wt-% indium to determine whether this high selectivity catalyst would also have sustained activity for selective hydrogenation. Operating conditions for the sustained activity tests included: reactor pressure of 150 psig; 1.5 wt-% acetylene was absorbed and dissolved in the NMP absorbent to provide the reactant stream; the molar ratio of H$_2$ to C$_2$H$_2$ was set at 1.26:1; and the flowrate of reactant through the bed (liquid hourly space velocity) was set to an LHSV of 5 hr$^{-1}$.

The catalyst was operated for about 143 hours, and product gas composition was determined at selected intervals, as shown in Table 2. It is estimated that the mass balance closure for these results was about 95%.

TABLE 2

| Time on Stream (hrs) | 70 | 104 |
|---|---|---|
| Temperature (° C.) | 134 | 134 |
| Pressure (psig) | 150 | 150 |
| Methane (wt-%) | 0.01 | 0.01 |
| Ethane (wt-%) | 1.30 | 1.19 |
| Ethylene (wt-%) | 97.50 | 98.10 |
| Acetylene (wt-%) | 0.39 | 0.08 |
| Trans-2-butene (wt-%) | 0.07 | 0.06 |
| 1-butene (wt-%) | 0.21 | 0.17 |
| Cis-2-butene (wt-%) | 0.07 | 0.06 |
| Butadiene (wt-%) | 0.40 | 0.31 |
| Total (wt-%) | 99.95 | 99.98 |
| S$_s$ | 75 | 82 |
| S$_c$ (%) | 99.6 | 99.9 |

After this extended run, the catalyst bed was flushed with nitrogen at 425° C. and the catalyst was oxidized in air for one hour. The catalyst was then reduced with the 2:1 H$_2$:CO mixture at 417° C. and 150 psig, and tested again to determine whether it was active. The catalyst was again both active and selective for the selective hydrogenation of acetylene dissolved in NMP with a H$_2$ and CO mixture.

Selective Hydrogenation of Acetylene—Zinc-Promoted Palladium Catalyst

Example 13

This example was performed under conditions similar to those of Example 11, using the catalyst prepared as described in Example 10. The reactant stream comprised 1.5 wt-% acetylene in NMP. The H$_2$:CO feed ratio was 2:1 (vol/vol). The H$_2$:C$_2$H$_2$ to the reactor was 2.76:1. The reaction pressure was maintained at approximately 250 psig and the average temperature in the catalyst bed was 128° C. The reactant stream flow rate was set to a LHSV of 5 hr$^{-1}$.

Table 3 provides results from these tests in the form of product gas composition as a function of reaction time. It is estimated that the mass balance closure for these results was about 98-99%. As will be seen from the results in Table 3, the process of the present invention provides improved ethylene selectivity at high acetylene conversion with the zinc-promoted catalyst.

TABLE 3

| Time (hr) | CH$_4$ (wt-%) | C$_2$H$_6$ (wt-%) | C$_2$H$_4$ (wt-%) | C$_2$H$_2$ (wt-%) | t-C$_4$H$_8$ (wt-%) | i-C$_4$H$_8$ (wt-%) | c-C$_4$H$_8$ (wt-%) | 1,3-C$_4$H$_8$ (wt-%) | S$_s$ | S$_c$ (%) |
|---|---|---|---|---|---|---|---|---|---|---|
| 0.5 | 0.04 | 0.91 | 97.4 | 0.48 | 0.04 | 0.09 | 0.07 | 0.85 | 107 | 99.5 |
| 1.0 | 0.02 | 0.87 | 97.4 | 0.37 | 0.05 | 0.09 | 0.08 | 1.00 | 112 | 99.6 |
| 1.5 | 0.02 | 0.85 | 97.5 | 0.29 | 0.05 | 0.09 | 0.07 | 1.00 | 115 | 99.7 |
| 2.0 | 0.01 | 0.84 | 97.6 | 0.24 | 0.04 | 0.09 | 0.07 | 1.00 | 115 | 99.8 |
| 2.5 | 0.01 | 0.83 | 97.7 | 0.21 | 0.04 | 0.08 | 0.06 | 0.97 | 118 | 99.8 |
| 3.0 | 0.01 | 0.82 | 97.8 | 0.20 | 0.04 | 0.08 | 0.06 | 0.93 | 119 | 99.8 |
| 3.5 | 0.01 | 0.81 | 97.9 | 0.18 | 0.04 | 0.07 | 0.06 | 0.89 | 121 | 99.8 |
| 4.0 | 0.01 | 0.81 | 98.0 | 0.16 | 0.03 | 0.07 | 0.05 | 0.83 | 121 | 99.8 |
| 4.5 | 0.01 | 0.80 | 98.1 | 0.14 | 0.03 | 0.07 | 0.05 | 0.77 | 123 | 99.9 |
| 5.0 | 0.01 | 0.79 | 98.2 | 0.12 | 0.03 | 0.06 | 0.04 | 0.72 | 124 | 99.9 |

Selective Hydrogenation of Acetylene—Sustained Activity of Zinc-Promoted Palladium Catalyst Example 14

This example was again performed using the catalyst of Example 10. The test was performed under conditions similar to those of Example 13 but with the following differences. The reactant stream flow rate was set to a LHSV of 10 hr$^{-1}$. The average catalyst bed temperature was 140° C., and the $H_2:C_2H_2$ to the reactor was 3.7:1.

The results of this test are provided in Table 4 in the form of gas composition. The gas composition data are the result of gas analyses only; when the $C_4$ compounds that collect in the liquid are combined with those in the gas phase, 3.14 wt-% of the acetylene reacted goes to form $C_4$ compounds initially, but this FIGURE drops to 2.31 wt-% after 14 hours of operation and levels off to about 2.1 wt-% after about 21 hours of operation. It is estimated that the mass balance closure for these results was about 98%-99%.

Accordingly, the progressive decline in activity with time on stream predicted by the conventional art is not observed with the process of the present invention. Indeed, the results of Table 3 indicate improvement in conversion and selectivity with time on stream for the inventive process using the catalyst of Example 10.

TABLE 4

| Time (hr) | $CH_4$ (wt-%) | $C_2H_6$ (wt-%) | $C_2H_4$ (wt-%) | $C_2H_2$ (wt-%) | $C_4H_8$ (wt-%) | $1,3-C_4H_8$ (wt-%) | $S_s$ | $S_c$ (%) |
|---|---|---|---|---|---|---|---|---|
| 7 | 0.06 | 0.33 | 97.4 | 1.20 | 0.07 | 0.87 | 295 | 98.8 |
| 14 | 0.07 | 0.60 | 98.1 | 0.68 | 0.10 | 0.43 | 164 | 99.3 |
| 21 | 0.02 | 0.60 | 98.2 | 0.77 | 0.02 | 0.31 | 164 | 99.2 |
| 24 | 0.02 | 0.50 | 98.6 | 0.33 | 0.02 | 0.38 | 197 | 99.7 |

The examples provided in the disclosure are presented for illustration and explanation purposes only and are not intended to limit the claims or embodiment of this invention. While the preferred embodiments of the invention have been shown and described, modification thereof can be made by one skilled in the art without departing from the spirit and teachings of the invention. Process design criteria, pendant processing equipment, and the like for any given implementation of the invention will be readily ascertainable to one of skill in the art based upon the disclosure herein. The embodiments described herein are exemplary only, and are not intended to be limiting. Many variations and modifications of the invention disclosed herein are possible and are within the scope of the invention. Use of the term "optionally" with respect to any element of the invention is intended to mean that the subject element is required, or alternatively, is not required. Both alternatives are intended to be within the scope of the invention.

The discussion of a reference in the Description of the Related Art is not an admission that it is prior art to the present invention, especially any reference that may have a publication date after the priority date of this application. The disclosures of all patents, patent applications and publications cited herein are hereby incorporated herein by reference in their entirety, to the extent that they provide exemplary, procedural, or other details supplementary to those set forth herein.

What is claimed is:

1. A process for selective hydrogenation comprising:
    absorbing one or more acetylenic compounds in a liquid polar non-hydrocarbon absorbent to provide a reactant stream;
    providing a hydrogenation catalyst comprising a first metal selected from the group consisting of Group VIII metals and combinations thereof and a second metal selected from the group consisting of Group IB metals, Group IIB metals, Group IIIA metals, Group VIIB metals, and combinations thereof;
    contacting the reactant stream with the hydrogenation catalyst, in the presence of a gas stream comprising hydrogen and greater than 2000 ppm carbon monoxide, under selective hydrogenation conditions, to provide a product stream;
    wherein the product stream comprises the ethylenic compounds corresponding to the one or more acetylenic compounds in the reactant stream; and
    separating the absorbent from the product stream.

2. The process of claim 1 wherein the hydrogenation catalyst comprises from about 0.01 weight percent to about 10 weight percent of the first metal.

3. The process of claim 2 wherein the hydrogenation catalyst comprises from about 0.01 weight percent to about 10 weight percent of the second metal.

4. The process of claim 1 wherein the second metal is selected from the group consisting of Group IIB metals, Group IIIA metals, Group VIIB metals, and combinations thereof.

5. The process of claim 4 wherein the second metal is selected from the group consisting of In, Ga, Mn, Zn, and combinations thereof.

6. The process of claim 4 wherein the catalyst further comprises an alumina support, the first metal comprises palladium and the second metal comprises zinc.

7. The process of claim 4 wherein the catalyst further comprises an alumina support, the first metal comprises palladium and the second metal comprises manganese.

8. The process of claim 1 wherein the catalyst is produced by impregnating a precursor with the second metal, wherein the precursor comprises from about 0.01 weight percent to about 10 weight percent of the first metal disposed on an inorganic support.

9. The process of claim 8 wherein the precursor is impregnated with the second metal by contacting the precursor with a solution selected from metal chloride solutions, metal acetate solutions, metal formate solutions, metal nitrate solutions, and combinations thereof.

10. The process of claim 9 wherein the solution is selected from the group consisting of gold chloride, zinc formate, silver nitrate, manganese acetate, indium nitrate, gallium nitrate, and combinations thereof.

11. The process of claim 1 wherein the gas stream comprises from about 0.01 percent to about 300 percent of the stoichiometrically required amount of hydrogen.

12. The process of claim 1 wherein the selective hydrogenation conditions comprise a temperature of from 100° C. to 150° C., a pressure of from 100 psig to 400 psig, a $H_2$:CO mole ratio of from about 1:1 to about 3:1, and a $H_2$:ethlynic mole ratio of from about 1:1 to about 5:1.

13. The process of claim 1 wherein the catalyst is capable of selectively hydrogenating acetylene with a conversion $S_c$ of at least about 90% and a selectivity to ethylene relative to ethane $S_s$ of at least about 20 when the catalyst is employed in a steady-state liquid phase hydrogenation process.

14. The process of claim 8, wherein the catalyst has a minimum dimension in the range of from about 0.01 inch to about 0.02 inch.

15. The process of claim 8, wherein the inorganic support has a size greater than the minimum dimension, and the impregnated precursor is comminuted to achieve the minimum dimension.

16. The process of claim 1, wherein the catalyst is capable of sustained activity for acetylene hydrogenation for at least about 100 hours.

* * * * *